United States Patent [19]

Schepers

[11] 4,272,431

[45] Jun. 9, 1981

[54] PROCESS FOR PREPARING A POLYMER MIXTURE

[75] Inventor: Herman A. J. Schepers, Stein, Netherlands

[73] Assignee: Stamicarbon, B.V., Geleen, Netherlands; 4

[21] Appl. No.: 89,358

[22] Filed: Oct. 30, 1979
(Under 37 CFR 1.47)

Related U.S. Application Data

[63] Continuation of Ser. No. 835,893, Sep. 23, 1977, abandoned.

[30] Foreign Application Priority Data

Sep. 25, 1976 [NL] Netherlands ........................ 7610672
Sep. 25, 1976 [NL] Netherlands ........................ 7610674

[51] Int. Cl.$^3$ ........................ C08K 3/04; C08L 53/00
[52] U.S. Cl. ........................ 260/42.46; 260/23.5 R; 260/23.5 A; 260/42.47; 525/88; 525/96; 525/97
[58] Field of Search ................ 525/88, 97; 260/42.46, 260/42.47, 23.5

[56] References Cited

U.S. PATENT DOCUMENTS

| | | | |
|---|---|---|---|
| 3,354,239 | 11/1967 | Short | 525/84 |
| 3,767,613 | 10/1973 | Dix et al. | 260/42.45 |
| 3,906,056 | 9/1975 | Okamoto et al. | 525/97 |

Primary Examiner—J. Ziegler
Attorney, Agent, or Firm—Cushman, Darby & Cushman

[57] ABSTRACT

A new elastomeric composition is described, having an improved combination of characteristics, which is composed of an intimate admixture of (a) 25–85% by weight of a substantially amorphous ethene-α-alkene copolymer, having a relatively low X-ray crystallinity of below about 4% by weight; and a tensile strength of at least 10 kg/cm$^2$, and (b) 15–75% by weight of an at least partially crystalline block copolymer of propene and ethene, having an ethene content of between about 1 and 25% by weight and relatively high X-ray crystallinity of at least about 25% by weight.

33 Claims, No Drawings

PROCESS FOR PREPARING A POLYMER MIXTURE

CROSS-REFERENCE TO RELATED APPLICATIONS

This application is a continuation of my earlier application Ser. No. 835,893 filed Sept. 23, 1977, now abandoned.

This invention relates to a process for preparing a thermoplastic, elastomeric mixture composition composed of polyalkene copolymer rubber and a thermoplastic polyalkene block copolymer, and to the process of making the same.

BACKGROUND OF THE INVENTION

In U.S. Pat. No. 3,758,643 (Netherlands Patent Application No. 72 00773), it has been taught that there can be prepared a composition composed of a rubbery ethene-propene copolymer and a thermoplastic polyolefin polymer (such as a polypropylene homopolymer copolymer). The said rubbery ethene-propene copolymer of the EPDM-type may include one or more copolymerized unconjugated dienes, such as dicyclopentadiene, ethylidene norbornene and cyclooctadiene. In such preparation, the polyalkene rubber (e.g., an EPDM rubber) must have been partly cured by means of a suitable curing agent before it is mixed with the thermoplastic polyalkene. That is, prior to said mixing, some chemical cross-linking must already have been developed in this rubbery copolymer component. These rubbery mixtures can then be processed into useful thermoplastic plastomeric molded or extruded articles without requiring further vulcanization treatment.

However, such practice, requiring the initial partial cross-linking of the rubbery ethene-propene polymer has certain disadvantages. Both the polymer itself and also the mixtures containing the partly cross-linked polymer are somewhat difficult to process. Moreover, the requirement for the additional step of initial, partial cross-linking in the process adds to the manufacturing expense of the resulting mixtures. Furthermore, the use of cross-linking agents has itself a number of disadvantages that are well known to the expert, such as toxicity of the agents, and, especially when peroxides are used, the odor and/or explosion hazard presented.

Further, from the U.S. Pat. No. 3,919,358, it is also well known to prepare composition composed of mixtures of a crystalling EPDM polymer and a polyethene polymer. The EPDM polymer is there to have a crystallinity of about 10 to 20% by weight. However, these mixture compositions have a low stiffness, a low hardness and unsatisfactory elastic properties; in particular the permanent deformation characteristics thereof are high. Further, the temperature resistance of such compositions is limited, and, as a result, these mixtures are unsuitable for some applications in which higher temperatures may occur.

So far, it has, in general, been thought that the characteristics of good elastomeric properties and of relatively easy processability in polymer compositions were mutually exclusive in polymer compositions. Generally, it has been thought that with elastomeric polymer products, good elastic properties could be achieved along with ease of processing, only by making use of physical cross-linking, e.g., that kind of cross-linking which dissipates upon heating the material above its vitrification point, so that the material can then be processed, and which then re-appears upon cooling of the material below its vitrification point. Those styrene block copolymers which are based on styrene (S) and a conjugated diene (B), and of the general formula $S(B\ S)_n$, where $n \geq 1$, are good examples of this kind of polymers, and are already being prepared on a large scale.

According to the present invention, it has now been found that when use is made of certain specific, substantially amorphous unvulcanized ethene-α-alkene copolymers and certain polypropene block copolymers, polymer mixture compositions can then be obtained which do have both the desirable combined characteristics of good elastic properties with relatively easy processability.

OBJECTS OF THE PRESENT INVENTION

Accordingly, the principal object of this invention is to provide new and novel thermoplastic elastomers which possess good processability, along with good mechanical and elastic properties, and which can be prepared in a simple way.

Another object of the invention is to provide thermoplastic elastomers that which are useful over a wide temperature range and which have improved resistance to deterioration caused by aging and weather conditions.

The compositions of the present invention do not rely on a physical cross-linking, but nonetheless combine the closely approximate elastic properties and the processing characteristics of the aforementioned styrene block copolymers with the other useful properties thereof being at least equivalent therewith. The further advantages of the present composition mixtures over the prior styrene block copolymers include: (a) lower cost price (the preparation of the styrene block copolymers is complicated and requires great care), (b) improved weather resistance (the polydiene middle block of the prior block copolymers is extremely susceptible to aging), and (c) improved heat resistance (at 90° C. the strength of the prior art styrene block copolymers has almost completely disappeared).

According to this invention, novel elastomeric polymeric composition mixtures are provided which essentially consists of 1. About 25 to 85% by weight of a substantially amorphous ethene-α-alkene copolymer having a crystallinity of at most about 4% by weight and a tensile strength of at least about 10 kg/cm², and 2. About 15 to 75% by weight of a substantially crystalline block copolymer of propene and ethene, with an ethene content therein of between about 1 and 25% by weight, and a crystallinity of at least about 25% by weight. Preferably, the mixtures contain from 30 to 65% by weight of the crystalline propene-ethene block copolymer.

The resulting compositions including these propene block copolymers have an improved processability and a higher tensile strength than compositions in which mere propene or ethene homopolymers have been incorporated. Improved elastic properties are also obtained.

While the processes for making the components of the present inventive compositions are themselves generally already known, the following descriptions will aid in understanding the present invention.

BLOCK COPOLYMER DESCRIPTION

The crystalline propene/ethene block copolymers used herein, notably the so-called reactor block copolymers, can be prepared by processes which are themselves already well known in the art.

In these processes, the reaction is generally carried out in a diluent, which diluent may be the liquid propene monomer itself if so desired. A titanium-trichloride compound is generally used as the principal polymerization catalyst. This catalyst may be prepared either by reduction of titanium tetrachloride and/or by grinding crystalline titanium trichloride. Other substances may be added, thereto, as desired, to increase the activity and/or the stereospecificity of the catalyst. Thus, prior to conducting the polymerization reaction, a so-called activator may be added, which may be a metal-organic compound or a metal hydride of a metal from the groups I, II and/or III of the Periodic Table, in particular lithium, sodium, zinc, magnesium, and most preferably, aluminum. Some examples of such activators are aluminum triethyl, diethyl aluminum chloride, ethyl aluminum dichloride, dibutyl magnesium, ethyl magnesium bromide, calcium hydride, butyl lithium, diethyl zinc, lithium aluminum hydride, and mixtures thereof. Suitable additives for raising the stereospecificity are, i.e., ethers, esters and alcoholates, tertiary amines and hydrides.

The preparation of the propene block copolymers for use herein is preferably started by first forming a substantially homopolymer of propene, to obtain a crystalline propene polymer block having a crystallinity of at least about 40%. Thereafter, ethene is introduced to form a substantially ethene homopolymer block. The sequential cycle of propene polymerization and ethene polymerization may be repeated several times as desired, to form a multiple block copolymer.

During formation of the ethene polymer block, the polymerization reactor is advantageously completely or at least substantially freed from unconverted propene monomer, before the ethene is added. This may be done by allowing the compressed propene therein to escape from the polymerization reactor and/or by cutting off addition of fresh propene while allowing the initial propene polymerization, to continue until the propene within the reactor is substantially consumed.

To obtain the mixture of the present invention, preference is, however, given to those block copolymers which have been so prepared that the polyethene block itself contains from about 0.1% up to about 15% by weight, in particular from about 0.5% up to about 10% by weight, of propene co-monomer therein. This may be achieved by adding the appropriate amount of propene along with the ethene monomer after formation of the polypropene block. The ethene polymer block formation may also be carried out partly as a copolymerization with propene remaining in the reactor and partly as ethene homopolymerization.

However, when the propene block polymerization phase is followed by the polymerization of a mixture of ethene and propene, it is still preferably to remove all, or at least part, of the unconverted propene monomer previously in the reactor.

If so desired, the polypropene block may also contain small amounts of ethene co-monomer. Thus, it is possible to use an ethene monomer feed of about 1 to 3% by volume during all or part of propene polymerization phase. But, preferably, the polypropene block is present as a homopolymer block.

During all or part of the duration of the respective block polymerization phases, but especially during the (homo)polymerization of the propene block, hydrogen may be introduced for control of the molecular weight of the block being formed.

For use herein, the total ethene content of the final block copolymer should be from about 1 to 25%, preferably 2.5 to 15%, and, most preferably, about 5 to about 10% by weight thereof.

Block copolymers with a so-called disturbed polyethene block, i.e., those in which propene has been polymerized together with the ethene, are to be preferred because of the interactions which apparently subsequently occur with the substantially amorphous copolymer of ethene and α-alkene. These interactions appear to affect very favorably the mechanical properties of the final composition.

In forming the mixtures according to this invention, block copolymers having a melt index (measured according to ASTM- D-1238 at 230° C., 2.16 kg) of between 0.1 and 20 dg/min., in particular of between 0.5 and 10 dg/min., are preferably used. These values lead to the best compromises between mechanical properties and processability.

The block copolymers used in this invention are also substantially insoluble in boiling hexane, that is, only a minor amount of the block copolymer will thus dissolve. The amount of thus-soluble polymer should be less than about 20% by weight, in particular less than about 10% by weight, of the total block copolymer.

RUBBERY ETHENE-α-ALKENE COPOLYMER DESCRIPTION

The amorphous rubbery ethene-α-alkene copolymer is preferably a so-called EP or EPDM rubber, consisting essentially of a copolymer of ethene and propene, along with one or more polyenes, such as dienes and trienes, as may be desired.

The copolymers are prepared by interpolymerization of a mixture of ethene, at least one other α-alkene, and, optionally, at least one polyene, using a coordination catalyst. Either an organic solvent solution or suspension technique may be used.

The coordination catalyst used is already known in the art may be formed by combining at least one heavy metal component compound of a metal from sub-groups 4 through 6 or 8 of Mendeleev's Periodic Table, including thorium and uranium, with a metal, alloy, metal hydride or metal compound of a metal from groups 1 through 3 or from the fourth group of said Periodic Table, i.e., the so-called aluminum component. Other substances may also be included, such a minor amount of compounds having a free pair of electrons, e.g., water, alcohol, oxygen, or Lewis bases, or, also, minor amounts of polyhalogenated organic compounds.

Preferably, the catalyst system is formed by combining a soluble vanadium and/or titanium compound, e.g., vanadium oxytrichloride and/or vanadium tetrachloride and/or titanium tetrachloride and/or tetra-alkyl titanate, with one or more (preferably organic) aluminum compounds, such as aluminum trialkyls, dialkyl aluminum halogenide and/or mono-alkyl aluminum halogenide, dialkyl aluminum monohydride. Preferably, those aluminum lower alkyl compounds having an alkyl group of 2 to 8, in particular 2 to 5, carbon atoms, are used.

In such catalyst systems, the molar ratio of the aluminum component to the heavy-metal component may be varied within wide limits, e.g., between 2:1 and 500:1, and, preferably, between 3:1 and 25:1. When the process is carried out continuously, the catalyst components may be fed directly to the polymerization zone as a solution in the reaction solvent.

Very good results are obtained using the combination of vanadium oxytrichloride and alkyl aluminum halogenides.

The co-monomer in the ethene copolymer may be any copolymerizable $\alpha$-alkene, but preferably those having from 3 to 18 carbon atoms per molecule, and especially those having from 3 to 4 carbon atoms per molecule. Some examples of $\alpha$-alkene co-monomers are butene, 4-methyl pentene-1, hexene, heptene, and especially propene. Mixtures of $\alpha$-alkenes co-monomers such as, e.g., propene and butene, may also be used.

As the polyene co-monomer component there are preferably used non-conjugated dienes, such a dicyclopentadiene, 1,4-hexadiene, 1,5-hexadiene, ethylidene norbornene, or norbornadiene. In general, dienes with from 4 to 16 carbon atoms, in particular from 6 to 12 carbon atoms are suitable. The most preferred diene co-monomers are dicyclopentadiene, ethylidene norbornene, and 1,4-hexadiene, which may optionally be used in combination with norbornadiene.

Normally, the ethene-$\alpha$-alkene copolymerization reaction is carried out at a temperature of between about $-40°$ and $120°$ C., preferably between about $-20°$ and about $80°$ C. The pressure will normally be from 1 to about 50 atmospheres, but higher or lower pressures may also be used. The process is preferably effected continuously.

The reaction diluent or solvent used may be any organic liquid that is inert with respect to the catalyst used. Preferably, an aliphatically-saturated hydrocarbon having from 4 to 18 carbon atoms per molecule is used for this purpose.

Some examples of useful hydrocarbons are the saturated aliphatic and cycloaliphatic hydrocarbons, such as butane, pentane, cyclohexane, hexane, heptane, or petroleum fractions; benzene and lower alkaryls, e.g., toluene, may also be used. Halogenated organic hydrocarbons, such as tetrachloroethene are also useful.

Advantageously, the reaction is conducted under conditions of temperature and pressure such that one or more of the monomers used, especially the $\alpha$-alkene co-monomer (e.g., propene), is in the liquid state, and present also in sufficient amount to serve itself as the reaction diluent. Another diluent is then not necessary.

The molecular weight of the copolymers to be used in this invention can generally be influenced by the presence of chain regulators, such as, e.g., acetylene, hydrogen, butadiene-1,2, zinc alkyls, and alkyl halogenides. Hydrogen is the preferred chain regulator. The molecular weights of the rubbery copolymers usually range between $5 \times 10^4$ and $1 \times 10^6$. Molecular weight here denotes the weight-average molecular weight as measured by the light-scattering technique, after removal of gel if any.

According to the invention, the copolymers employed should have a tensile strength of at least 10 kg/cm$^2$ in the unvulcanized condition (so-called green strength); however, values thereof of over 50 kg/cm$^2$ are preferred.

Furthermore, it has been found herein that thermoplastic elastomer mixtures having good mechanical properties, particularly a high value of elongation at rupture and which are readily processable at relatively low expenditure of energy can be prepared by incorporating an amount of oil in the polymer mixtures.

Preferably, the oil is incorporated in the mixture in an amount of 20 to 200 parts of oil, most preferably about 25 to about 150 parts, per 100 parts by weight of rubbery copolymer component thereof.

While the incorporation of oil in rubbers intended to be vulcanized in a long-standing measure, these oil extended rubbers generally show considerably poorer mechanical properties in the unvulcanized state than the extended rubbers. Not until after vulcanization do the properties of the oil extended rubber reach a level that can be compared to that of unextended rubbers. However, no vulcanization is required in the practice of the present invention.

Mixing crystalline polymers with oil does not give any advantage as regards the mechanical properties; on the contrary, the incorporation of oil generally has strongly negative effect on the mechanical properties.

The mixtures obtained by this invention, consisting essentially of a crystalline propene block polymer and a rubbery ethene-$\alpha$-alkene copolymer appear to display a kind of synergism in respect of their various properties, such as mechanical and elastic properties, processability and heat-resistance, which effect can only be ascribed to the interactions that occur between the components of the mixture. To retain these favorable combined properties, it has normally been necessary to avoid any measure which might disturb the combined action of the components of polymer mixtures.

Hence, it is contrary to all expectation that both the elastic properties and the processability of the present mixtures are strongly improved by incorporation of an oil in the mixture of crystalline propene block copolymer and rubbery ethene-$\alpha$-alkene copolymer. The other properties moreover, remain virtually unchanged.

The addition of oil is particularly attractive herein when mixtures are used in which over 50 parts of propene block copolymer per 100 parts of the rubber ethene-$\alpha$-alkene copolymer have been incorporated. The magnitude of the tensile strength in the unvulcanized condition sharply increases as the ethene content of the copolymer is increased. However, if the ethene content therein is too high, the elastic properties decrease.

Therefore, those ethene-$\alpha$-alkene copolymers having an ethene content of between 60 and 80% by weight, in particular between about 62 and about 70% by weight, are preferred. While the rubbery copolymers used must have a high tensile strength according to the invention, good processability properties are also required. In other words, the viscosity of the rubbery copolymers must not be too high. A Mooney viscosity 125° $(1+4)$ ranging between about 30 and about 100 is preferred. At lower values the elastic behavior and the mechanical strength deteriorate; at higher values the processability of the polymer is considerably worsened. In case an oil is incorporated in the mixture according to the invention, the mixture of the rubbery copolymer and oil must also have a Mooney viscosity ranging between 30 and 100.

A content of crystalline polymer of less than about 4% by weight in the substantially amorphous copolymer is required according to the invention, preferably lower than about 2.5% by weight, and most preferably below about 1% by weight.

In its most preferable form, the amorphous ethene-α-alkene copolymer exhibits a crystallinity that is hardly or not at all detectable, e.g., less than 0.25%.

Unless stated otherwise, crystallinity as used herein denotes the crystallinity measured at room temperature by means of the well-known X-ray techniques. Due to these low crystallinity values, the elastic properties of the mixtures are high.

For best results, use is recommended of an amorphous ethene-α-alkene copolymer having a differential-scanning (d.sc.)-crystallization temperature of over +0° C., in particular over +5° C., and a heat of crystallization, measured by the d.sc. technique, of at least 6 cals/g. in particular at least 7 cals/g.

In effect, the amorphous ethene-α-alkene copolymer must preferably contain at most very little X-ray crystallinity, but it must nonetheless contain a certain amount of crystallizable polymer measured by the d.sc. technique.

D.Sc. crystallization temperatures above 50° C. do not tend to improve the properties of the mixture, probably because the long ethene sequences which may be related to this crystallization do not give the desired favorable interactions with the polypropene block copolymer component. Therefore, it is even to be preferred that no d.sc. crystallinity can be detected above 50° C. Hence, the initiation of crystallization measured by means of d.sc. is preferably at or below 50° C.

The d.sc. curves were measured by means of a Perkin Elmer "differential-scanning" calorimeter, known by the trade name: Perkin Elmer DSC 2. Ethene-α-alkene copolymer samples of about 24 mg. were heated to 180° C. before being measured. The d.sc. crystallization thermogram was determined at a cooling rate of 5° C. per minute.

To carry out the measurements mentioned in this patent application, the temperature scale of the differential-scanning calorimeter had been calibrated, as is customary, by means of a number of reference substances. The melting temperatures obtained by heating these compounds at the rate of 5° C./min. were put equal to the equilibrium temperatures.

PREPARATION OF THE COMPOSITIONS

The mixture compositions of this invention may be prepared in the ways well known in themselves for various rubbers and plastics by means of conventional equipment, such as rollers, extruders, rapid mixers and kneaders, in which the material is subjected to shear forces at elevated temperature, in particular temperatures between about 170° and 200° C. For production on larger scales, preference is given to kneaders and extruders, in which the mixing is effected at temperatures of about 175° to about 190° C. The etheneα-copolymer is blended in an amount between about 25 and 85% by weight, and the propene block copolymer is blended in in an amount between about 15 and 75% by weight.

An improvement of the modulus (measured at 300% elongation) of the desired mixture can be achieved by replacing part of the rubbery ethene copolymer in the mixture by a halogenated EPDM rubber. This halogenated EPDM copolymer is preferably prepared by means of the process described in U.S. Pat. No. 3,936,430.

Various well-known additives, such as pigments, lubricants, fillers, antioxidants, may also be admixed into the present thermoplastic elastomeric mixtures without loss of the specific properties thereof. Carbon black, in particular, about 1 to 100, parts per 100 parts of polymer mixture.

As the mixtures according to the present invention can be made to vary from soft and rubbery to stiff and impact-resistance, they can be made for a wide variety of uses. They may also be mixed with other synthetic polymers. Reinforcing agents, such as fibers, may be incoporated in them, and they may be provided with a coating, such as paint or lacquer. Particularly good results are obtained by additionally incorporating polyethene in an amount of up to about 20% by weight, especially between about 5 and 15% by weight. In this case, polyethene having a density of at least 0.950 is preferably used.

The mixtures are particularly suitable for the manufacture of cable sheaths and automobile bumpers.

EXAMPLE 1

An EPDM rubber and a polypropane block copolymer were mixed in various ratios (see below) on an open roller. The roller temperature was +190° C. The EPDM rubber was first rolled into a sheet, after which the polypropane block copolymer (PPB) was added, with a total mixing time of 9 minutes.

The EPDM rubber used in this Example was constituted of ethene, propene, and ethylidene norbornene and had the following characteristics:

| | |
|---|---|
| Ethene content | 64.0% by weight |
| Ethylidene-norbornene content | 7.8% |
| Mooney (1 + 4) at 125° C. | 62 |
| Heat of crystallization | 10.5 cals/g (d.sc.) |
| DSC peak temperature | +17° C. |
| Initiation of crystallization | +49° C. (d.sc.) |
| X-ray Crystalline material | <0.25% |

The content of crystalline material was determined by mean of X-ray diffraction in the following way: Diffractograms were run on unoriented samples in the 8° to 32° range (Cu K α radiation) at room temperature. The content of crystalline material can be derived from the ratio between the area of the crystalline part to the total surface area under the curve.

The propene block copolymer (PPB) had been prepared as follows. First propane was homopolymerized in the presence of hydrogen; after the unconverted propene and hydrogen were removed, polymerization was then continued with ethene.

After deactivation and recovery, the propene block copolymer contained 7% by weight of ethene, of which 1% by weight was crystalline. The portion soluble in boiling hexane (duration 48 hours) was 2.6% by weight. The melt index (230° C., 2.16 kg weight) was 2.6 dg/minute. The content of crystalline polypropene was 43% by weight measured by the d.sc. method, and >50% by weight measured by X-ray determination.

Test specimens were then made of these mixtures by compression moulding at a temperature of +180° C. and a final pressure of 15 kg/cm². Cooling was effected at a pressure of 40 kg/cm². These specimens were then subjected to several measurements, for which the following specifications were used, unless stated otherwise:

1. Tensile test according to NEN 5602, type III test rod;
2. Hardness test according to ASTM D 2240, shore A hardness;

3. Mooney viscosity measurement ML (1+4) +125° C. according to ASTM D 1640-68;
4. Determination of melt index according to ASTM D 1238 at +190° C., 10 kg weight;
5. Determination of permanent elongation by stretching a test specimen by 75 or 200% for 24 hours and measuring the permanent deformation in percent of the original length one hour after release of stretch.

The properties of the mixtures are give in the following table for mixtures of the various ratios of parts by weight of the EPDM rubber (EPDM) and the above-described block copolymer (PPB).

TABLE I

| Mixture | Tensile Strength kg/cm² | Stiffness Modulus at 300% kg/cm² | Elongation at Rupture % | Hardness Shore A | Permanent Elongation % at 75% | Permanent Elongation % at 200% | Melt Index dg/min |
|---|---|---|---|---|---|---|---|
| 100 parts EPDM | 163 | 19 | 770 | 61 | 15 | 25 | 0.4 |
| 90 parts EPDM/ 10 parts PPB | 190 | 26 | 750 | 66 | 15 | 27 | 0.5 |
| 80 parts EPDM/ 20 parts PPB | 218 | 44 | 720 | 72 | 20 | 35 | 0.8 |
| 70 parts EPDM/ 30 parts PPB | 238 | 73 | 720 | 79 | 25 | 55 | 1.3 |
| 60 parts EPDM/ 40 parts PPB | 272 | 102 | 690 | 91 | 35 | 90 | 1.9 |
| 50 parts EPDM/ 50 parts PPB | 285 | 112 | 730 | 97 | 45 | 150 | 3.9 |
| 40 parts EPDM/ 60 parts PPB | 308 | 125 | 750 | 98 | 50 | 165 | 6.3 |

These results show that amounts of polypropene of 10 parts per 90 parts of EPDM or smaller amounts will hardly give any improvement of the stiffness modulus of the mixture as compared to the EPDM rubber itself.

Not until 20 parts of polypropene and, in particular, 30 parts of polypropene have been added, are useful values of stiffness, hardness and melt index are obtained in combination with an additional considerable increase of the tensile strength.

EXAMPLE 2

As in Example 1, mixtures were prepared from EPDM rubbers with a low tensile strength in the unvulcanized condition (compare 163 kg/cm² in Table I).

The characteristics of the unvulcanized EPDM rubbers, R₁ and R₂, were as follows:

|  | R₁ | R₂ |
|---|---|---|
| Tensile strength kg/cm² | 4 | 12 |
| Ethene content % by weight | 57 | 58 |
| Ethylidene norbornene % by weight | — | 4.5 |
| Dicyclopentadiene % by weight | 4.2 | — |
| D.Sc. peak temperature °C. | −25 | −20 |
| X-ray Crystalline material % by wt. | <0.25 | <0.25 |
| Mooney (1 + 4) +125° C. | 45 | 69 |

The mixtures were then made up of 70 parts of EPDM rubber and 30 parts of the polypropene block copolymer (PPB) of Example 1, by the procedure of Example 1.

The properties of the mixtures are given in Table II below. For the sake of comparison, the similar 70/30 ratio mixture from Example 1 is also included.

TABLE II

| | Tensile Strength kg/cm² | Rigidity at 300% kg/cm² | Elongation at Rupture % | Hardness Shore A | Permanent Elongation at 200% | Melt Index dg/min. |
|---|---|---|---|---|---|---|
| 70 parts EPDM R₁/30 parts PPB | 21 | 15 | 790 | 70 | 60 | 4.2 |
| 70 parts EPDM R₂/30 parts PPB | 46 | 34 | 670 | 75 | 65 | 2.0 |
| 70 parts EPDM/ 30 parts PPB (Table I) | 238 | 73 | 720 | 79 | 55 | 1.3 |

The results show that the use of EPDM rubbers with too low a green strength gives clearly inferior results to the results from the use of EPDM rubbers with a higher green strength.

EXAMPLE 3

Mixtures of an EPDM rubber and a propene homopolymer (PPH) were made as in Example 1.

The melt index of this polypropene homopolymer was 1.3 dg/min. (230° C., 2.16 kg). The EPDM rubber was the same as that in Example 1.

The resuts are given in Table III below, including for comparison some results from Table 1 using instead of a polypropene block copolymer (PPB).

TABLE III

|  | Tensile Strength kg/cm² | Rigidity at 300% kg/cm² | Elongation at Rupture % | Hardness Shore A | Permanent Elongation % 75% | Permanent Elongation % 200% | Melt Index dg/min |
|---|---|---|---|---|---|---|---|
| 70 parts EPDM/ 30 parts PPH | 206 | 69 | 780 | 82 | 25 | 65 | 1.0 |
| 50 parts EPDM/ 50 parts PPH | 270 | 113 | 750 | 98 | 50 | 160 | 2.6 |
| 70 parts EPDM/ 30 parts PPB | 238 | 73 | 720 | 79 | 25 | 55 | 1.3 |
| 50 parts EPDM/ 50 parts PPB | 285 | 112 | 730 | 97 | 45 | 150 | 3.9 |

These results show that higher tensile strengths and better elastic properties and also a better processability can be obtained by means of block-copolymeric polypropene (PPB).

EXAMPLE 4

Mixtures of various EPDM rubbers with block-copolymeric polypropene of Example 1 were made on a roller as in Example 1.

The various EPDM rubbers had the following characteristics:

Table IV below gives the results of the tests performed on the EPDM rubbers themselves and on the indicated mixtures made with them (ratios shown in parts by weight).

The results show that the amount of crystalline material in the EPDM rubber, measured by means of X-ray diffraction at room temperature, has a strong influence on the elastic properties. The best elastic properties, in combinations with high modulus improvement, are obtained with a degree of crystallinity below 2.5% by weight (A through H), especially below 0.25 by weight

EXAMPLE 4

|  | EPDM-Rubbers | | | | | | | | | |
|---|---|---|---|---|---|---|---|---|---|---|
|  | A | B | C | D | E | F | G | H | I | J |
| Ethene Content % by weight | 61.9 | 61.4 | 63.5 | 59.4 | 61.9 | 67.2 | 64.0 | 63.2 | 68.2 | 73.1 |
| DSC peak temperature °C. | +4 | +7 | +10 | +15 | +13 | +16 | +17 | +17 | +26 | +42 |
| Heat of crystallization cals/g | 6.2 | 5.6 | 11.0 | 6.0 | 7.1 | 7.5 | 10.5 | 9.4 | 11.0 | 15.1 |
| Initial crystallization, °C. | +26 | +28 | +75 | +38 | +27 | +38 | +49 | +49 | +38 | +55 |
| Crystalline Material % by wt. (X-ray) | 0.7 | 0.9 | 0.8 | 1.2 | 0.25 | 2 | 0.25 | 0.25 | 3 | 9 |
| C9* content % by weight | 4.9 | 5.3 | 5.1 | 5.7 | 8.0 | — | 6.8 | 7.5 | 4.1 | — |
| C10* content % by weight | — | — | — | — | — | 4.2 | — | — | — | — |
| C6* content % by weight | — | — | — | — | — | — | — | — | — | 2.0 |
| Mooney (1 + 4) +125° C. | 62 | 74 | 75 | 80 | 74 | 64 | 62 | 75 | 82 | 55 |

*C9 = ethylidene norbornene
*C10 = dicyclopentadiene
*C6 = hexadiene-1,4

(E, G, H).

TABLE IV

|  | Tensile Strength kg/cm² | Stiffness Modulus at 300% kg/cm² | Elongation At Rupture % | Hardness Shore A | Permanent Elongation 75% | Permanent Elongation 200% | Melt Index dg/min. |
|---|---|---|---|---|---|---|---|
| EPDM-A | 52 | 9 | 1700 | 49 | — | 40 | 0.1 |
| EPDM-A/PPB 70/30 | 73 | 48 | 1020 | 64 | — | 45 | 1.2 |
| EPDM-B | 72 | 14 | 1340 | 65 | 20 | 30 | 0.2 |
| EPDM-B/PPB 70/30 | 90 | 52 | 750 | 80 | 28 | 70 | 1.0 |
| EPDM-C | 125 | 16 | 1040 | 58 | 15 | 30 | 0.3 |
| EPDM-C/PPB 70/30 | 153 | 62 | 820 | 83 | 25 | 65 | 1.1 |
| EPDM-D | 96 | 18 | 750 | 58 | 20 | 60 | 0.2 |
| EPDM-D/PPB 70/30 | 114 | 48 | 700 | 80 | 30 | 105 | 1.0 |
| EPDM-E | 88 | 14 | 1160 | 59 | 15 | 45 | 0.05 |
| EPDM-E/PPB 70/30 | 135 | 54 | 880 | 79 | 20 | 80 | 0.7 |
| EPDM-F | 166 | 19 | 836 | 59 | — | 32 | 0.4 |
| EPDM-F/PPB 70/30 | 220 | 76 | 740 | 82 | — | 50 | 1.6 |
| EPDM-G | 163 | 19 | 770 | 61 | 15 | 25 | 0.4 |
| EPDM-G/PPB 70/30 | 238 | 73 | 720 | 79 | 25 | 55 | 1.3 |
| EPDM-H | 139 | 20 | 710 | 64 | — | 40 | 0.4 |
| EPDM-H/PPB 70/30 | 240 | 72 | 700 | 83 | 25 | 70 | 1.4 |
| EPDM-I | 186 | 34 | 640 | 69 | 35 | 90 | 0.2 |

TABLE IV-continued

|  | Tensile Strength kg/cm² | Stiffness Modulus at 300% kg/cm² | Elongation At Rupture % | Hardness Shore A | Permanent Elongation 75% | Permanent Elongation 200% | Melt Index dg/min. |
| --- | --- | --- | --- | --- | --- | --- | --- |
| EPDM-I/PPB 70/30 | 335 | 78 | 680 | 85 | 35 | 110 | 0.7 |
| EPDM-J | 241 | 35 | 670 | 79 | 30 | 135 | 1.0 |
| EPDM-J/PPB 70/30 | 348 | 88 | 700 | 89 | 40 | 135 | 2.0 |

It furthermore appears, however, that the rubber must contain a minimum amount of crystallizable material e.g.. over 7 cals./g measured by DSC, in order to obtain a high increase of the tensile strength after being mixed with block-copolymeric polypropene. (Compare, e.g., results with EPDM-D, at 6.0 cals./g., with those of EPDM-E, at 7.1 cals./g).

It also appears that too high an initial temperature of crystallization of the rubber, as measured by means of d.sc., has a detrimental effect on the tensile strength improvement of the elastic properties of the mixture, if the starting material is a rubbery ethene copolymer with a reasonably high (green) tensile strength. Thus, it is preferred to have the initial temperature of crystallization (d.sc.) for this material below about 50° C.

It furthermore appears that, to obtain a reasonable level of tensile strength, also the d.sc. crystallization peak temperature of the rubbery ethene copolymer must be sufficiently high (higher than 4° C.). (Compare with example 2).

EXAMPLE 5

Mixtures of an EPDM rubber with polypropene homopolymers (PPH) and with the block-copolymeric polypropene of Example 1 were prepared on a roller, as in Example 1.

The rubber used was rubber H of Example V.

The polypropene homopolymers differed in melt index, as follows:

PPH 1: 10 dg/min. (230° C., 2.16 kg)
PPH 2: 4.6 dg/min.
PPH 3: 1.3 dg/min.

The block-copolymeric polypropene (PPB) had a melt index of 2.6 dg/min. Testing of the mixtures gave the following results.

TABLE V

|  | Tensile Strength kg/cm² | Modulus at 300% kg/cm² | Elongation at Rupture % | Hardness Shore A | Permanent Elongation 200% | Melt Index dg/min. |
| --- | --- | --- | --- | --- | --- | --- |
| EPDM-H/PPH 1 60/40 | 158 | 92 | 670 | 95 | 135 | 6.4 |
| EPDM-H/PPH 2 60/40 | 242 | 100 | 740 | 93 | 135 | 2.9 |
| EPDM-H/PPH 3 60/40 | 265 | 112 | 700 | 95 | 135 | 1.3 |
| EPDM-H/PPB 60/40 | 284 | 102 | 720 | 93 | 105 | 2.4 |

It follows from these comparative results that the block copolymers provide better characteristics than even to the best homopolymers, particularly as to the optimum combination of tensile strength, elastic properties and processability.

EXAMPLE 6

As in Example 4, various propene block-copolymers (PPB) were mixed with EPDM rubber H in an EPDM-rubber/PPB combination at a weight ratio of 70/30.

Block copolymers I and II used herein were prepared in the same way as in Example 1.

Block copolymer III is different in that propene is added during the ethene polymerization phase, as a result of which about 5% of propene is incorporated within the polyethene block.

In block copolymer IV, a short growing homopolymeric polypronene block was first formed, after which some ethene was added, so that the polypropene block as a whole contained 2% by weight of ethene. After flashing of residual propene and ethene, additional ethene was next polymerized in the presence of some propene so that a polyethene block was then formed constituting 2% by weight of the total block copolymer and within which about 5% by weight was composed of propene units.

Further characteristics of these four block copolymers were:

| | Melt-Index 230° C., 2.16 kg dg/min. | Ethene Content w. % | Cryst. Polyethene % | Cryst. Polypropene w. % | Cryst. Polypropene (X-ray) w. % | Soluble in Hexane w. % |
| --- | --- | --- | --- | --- | --- | --- |
| PPB I | 2.6 | 7 | 1 | 43 | >50 | 2.6 |
| PPB II | 1.5 | 12 | 2 | 40 | >50 | 3.1 |
| PPB III | 5.6 | 6 | 1 | 45 | >50 | 3.0 |
| PPB IV | 3.7 | 4 | 1 | 45 | >50 | 2.9 |

The mechanical properties and the melt index of the 70/30 mixtures were measured. Table VI below lists the results.

TABLE VI

|  | Tensile Strength kg/cm² | Stiffness Modulus at 300% kg/cm² | Elongation at Rupture % | Hardness Shore A | Permanent Elongation 200% | Melt Index dg/min. |
| --- | --- | --- | --- | --- | --- | --- |
| EPDM-rubber H/PPB I | 240 | 72 | 700 | 83 | 60 | 1.4 |
| EPDM-rubber H/PPB II | 237 | 69 | 700 | 83 | 60 | 1.05 |
| EPDM-rubber H/PPB III | 242 | 75 | 700 | 84 | 50 | 1.4 |
| EPDM-rubber H/PPB IV | 200 | 70 | 670 | 83 | 70 | 1.0 |

These results show that block copolymers consisting of homopolymer block followed by a polyethene block, in which latter block some propene has been copolymerized PPB III, are to be preferred, as they give a still better combination of tensile strength, stiffness modulus, elastic behavior, hardness and processability. Note, however, the negative effects derived from PPB IV.

EXAMPLE 7

This Example shows the effect of the addition of a limited amount of chlorinated EPDM rubber on the properties of the mixture of EPDM and polypropene.

The polypropene and EPDM rubber used were the same as those described in Example 1.

The chlorinated (Cl-EPDM) was prepared in the way described in U.S. Pat. No. 3,936,430.

The mixture was prepared by mixing Cl-EPDM after the polypropene had been added. The total mixing time was 19 minutes.

The results of the tests are:

TABLE VII

|  | EPDM/PP 80/20 | EPDM/PP/Cl-EPDM 70/20/10 |
| --- | --- | --- |
| Tensile strength kg/cm² | 218 | 220 |
| Stiffness Modulus at 300% kg/cm² | 44 | 62 |
| Elongation at rupture % | 720 | 610 |
| Hardness Shore A | 72 | 74 |
| Permanent Elongation 200% | 35 | 34 |

These results show that the addition of chlorinated EPDM increases the rigidity, while the other properties generally remained at the same level.

EXAMPLE 8

Three mixtures were prepared in a kneader, consisting of EPDM-rubber, polypropene, polyethene and carbon black and having compositions as shown in the Table below.

The EPDM-rubber used (K) contained 63.5% by weight of ethene, 30% by weight of propene and 5% by weight of ethylidene norbornene. The tensile strength in unvulcanized condition amounted to 60 kg/cm². The Mooney plasticity (ML(1+4)125° C.) amounted to 52 and crystallinity was below 0.25%.

The propene polymer (PPBIII) is a block copolymer of propene and 6% ethene, having a density of 0.905 and a melt index (230° C./2.16 kg) of 5.6 dg/min, solubility in hexane 3% by weight, X-ray determined crystalline content of >50% by weight. This block copolymer was composed of a propene homopolymer block attached to an ethene copolymer block containing a small amount of propene.

The polyethene, denoted by PE in the following Table VIII has a density of 0.963 g/cm³ and a melt index of 8 dg/min. (190° C., 2.16 kg).

The experiments as described in the Table were carried out as follows: First the EPDM-rubber was fed to the kneader. After kneading for 1 minute the PP, PE and carbon black were added. After kneading for 4 minutes additional, kneading was carried out for 30 minutes without any sealant pressure, after which kneading was continued further until the temperature had risen to 165° C.

The mixture was injection molded to form plates, the properties of which were tested as indicated in Table VIII.

TABLE VIII

| Experiment No. | 1 | 2 | 3 |
| --- | --- | --- | --- |
| EPDM-K pts.-wt. | 25 | 25 | 25 |
| PPB III pts.-wt. | 75 | 65 | 60 |
| PE pts.-wt. | — | 10 | 15 |
| Carbon black pts.-wt. | 1 | 1 | 1 |
| Melt-Index (dg/min) | 15.7 | 12.7 | 11.4 |
| Hardness (Shore D) | 58 | 57 | 56 |
| Ram drop test crack energy (Nm) at −30° C. | 17.7 | 20.3 | 21.3 |
| Type of crack | tough | tough | tough |
| Ram drop test crack energy (Nm) at −40° C. | 16.3 | 18.5 | 18.4 |
| Type of crack | tough | tough | tough |

The properties listed were measured according to the following normal test procedures:

Melt Index: ASTM D-1238 (230° C./5 kg).
Hardness: ASTM D-2240 (reading after 3 sec.)
Ram drop test: Measured after conditioning at the indicated temperature for 48 hrs., by a 5 kg falling weight, dropped from a distance of 1 meter. The falling weight had a flat striking-surface of 1 cm diameter. The test plate of 5 mm thickness is supported by an annulus having a diameter of 2 cm.

From the table it appears that including polyethene in the mixture, up to about 25% based on the weight of the polypropene block copolymers, has a positive effect on the resulting toughness to cracking at low temperatures.

EXAMPLES 9–16

Mixtures were made of an ethene/propene/dicyclopendadiene terpolymer (terpolymer L) and a propene block copolymer (PPB III; see Example 8).

The characteristics of this terpolymer L were:

| Terpolymer L | |
| --- | --- |
| Ethene content | 67% by weight |
| Propene content | 29% by weight |
| Dicyclopentadiene content | 4% by weight |
| Tensile Strength | 120 kg/cm² |

-continued

| Terpolymer L | |
|---|---|
| Elongation at Rupture | 750% |
| Mooney viscosity ML (1 + 4) 120° C. | 140 |
| DSC peak temperature | + 15° C. |
| Heat of Crystallization | 7.0 cals/g |
| Content of Crystalline Material | 2.0% |

After 100 parts of terpolymer L were mixed with 100 parts of naphthene oil (Sunpar 2280), a Mooney viscosity ML(1+4) 120° C. of 36 was obtained. The tensile strength fell to 38 kg/cm² and the elongation at rupture was 1090%.

For the sake of comparison, mixtures were also made using an ethene/propene/ethylidene norbornene terpolymer (terpolymer M), the characteristics being:

| Terpolymer M | |
|---|---|
| Ethene content | 67% by weight |
| Propene content | 28% by weight |
| Ethylidene norbornene content | 5% by weight |
| Tensile Strength | 54 kg/cm² |
| Elongation at Rupture | 980% |
| Mooney viscosity ML(1 + 4) 125° C. | 54.5 |
| DSC peak temperature | + 15° C. |
| Heat of Crystallization | 10 cals/g |
| Content of Crystalline Material | 1.2% by weight |

The characteristics of the latter rubber (M) correspond as best as possible with those of the oil-extended rubber (L). As appears from the data given above, however, the rubber not extended with oil (M) shows the higher tensile strength and the higher Mooney viscosity compared with the oil-extended rubber.

Various mixtures were then made of the propene block copolymer (PPB III) with the oil-extended rubber (terpolymer L) and, for the sake of comparison, with terpolymer M.

The mixtures were prepared by mixing in a Brabender mixer at 180° C. for 10 minutes. The resulting products were then tested for a number of properties; the results obtained are compiled in the following Table IX.

and the compression set as compared to the non-oil-extended composition (10, 12, 14 and 16). The 300%-modulus and, especially, the tensile strength are generally lower, which is due to the lower initial values of the tensile strength and of the Mooney viscosity for the oil-extended terpolymer.

It is believed it will be clear to those skilled in the art from the foregoing Examples and general description of this invention that the novel compositions provided herein yield, on a comparative basis, unexpectedly improved useful elastomeric properties and conjoint characteristics which are associated with the particular combination of the described ethene-α-alkene copolymers of low crystallinity with a propene/ethene block copolymer of substantial crystallinity, as described above. As noted above, these two components in the mixture are physically mixed together, e.g., through kneading, with, of course, some elevation in the temperature occurring during the mechanical process, but without vulcanization or any required curing. Exactly why it should be that the improved characteristics are so obtained is not at this time clear. However, as pointed out hereinabove, there appears to be some advantageous, synergistic-like, interaction between the particular block copolymers used and the particular copolymers employed (within the above definitions) which provides these advantageous results.

Of course, the full scope of this invention is not limited to the particular compositions and formulations employed in the above Examples; variations thereof will be apparent to those skilled in the art from the above disclosure.

What is claimed is:

1. A thermoplastic, elastomeric composition based on a polyalkene rubber and a polyalkene plastic, and consisting essentially of an intimate mixture of
    (a) 25–85% by weight of a substantially amorphous ethene-α-alkene copolymer, having an X-ray crystallinity of below 4% by weight, a differential scanning (d. sc.) crystallization temperature of +0° to about 50° C. and a tensile strength in unvulcanized condition of at least 10 kg/cm², and
    (b) 15–75% by weight of an at least partially crystalline block copolymer of propene and ethene having an ethene content of between about 1 and 25% by weight and an X-ray crystallinity of at least 25% by weight.

TABLE IX

| Example No.: | 9 | 10 | 11 | 12 | 13 | 14 | 15 | 16 |
|---|---|---|---|---|---|---|---|---|
| PPB - III (parts by weight) | 20 | 20 | 30 | 30 | 40 | 40 | 60 | 60 |
| Terpolymer L | 80 | | 70 | | 60 | | 40 | |
| Terpolymer M | | 80 | | 70 | | 60 | | 40 |
| Melt Index dg/min. (ASTM D 1238 190° 10 kg) | 3.46 | 0.17 | 5.83 | 0.28 | 5.57 | 0.45 | 4.38 | 1.56 |
| Modulus (300%) in kg/cm² (NEN 5602 type 2) | 22 | 24 | 40 | 40 | 56 | 71 | 100 | 111 |
| Tensile strength in kg/cm² | 53 | 88 | 56 | 88 | 65 | 88 | 109 | 112 |
| Elongation at rupture in % | 1010 | 1070 | 610 | 850 | 450 | 530 | 410 | 330 |
| Permanent elongation after 200% elongation in % | 38 | 60 | 56 | 74 | 75 | 101 | 101 | 145 |
| Compression set 23° C. | 46 | — | 46 | — | 47 | — | 58 | 64 |
| 22 hrs. 70° C. | 83 | 98 | 80 | 96 | 81 | 95 | 78 | 95 |

These results show that the addition of oil (9, 11, 13, and 15) improves not only the processability, but also the elastic properties, notably the permanent elongation 2. The composition of claim 1, wherein the ethene content of the crystalline block copolymer is between about 2.5 to about 15% by weight.

3. The composition of claim 1, wherein the substantially amorphous ethene-α-alkene copolymer has a maximum crystallinity of about 2.5% by weight.

4. The composition of claim 1, wherein the amorphous ethene-α-alkene copolymer has an ethene content of between about 60 and about 80% by weight.

5. The composition of claim 1, wherein the ethene-α-alkene copolymer has a tensile strength of at least about 50 kg/cm$^2$.

6. The composition of claim 1, containing from about 30% to 65% by weight of the crystalline propene-ethene block copolymer.

7. The composition of claim 1, characterized in that the crystalline block copolymer or propene and ethene has been prepared by initial propene polymerization of propene, followed by ethene polymerization.

8. The composition of claim 7, wherein additional propene is copolymerized with the ethene.

9. The composition of claim 1, wherein the amorphous ethene-α-alkene copolymer is composed of ethene and propene.

10. The composition of claim 1, wherein the amorphous ethene-α-alkene copolymer is composed of ethene, propene, and a non-conjugated diene co-monomer.

11. The composition of claim 10, wherein the amorphous ethene-α-alkene copolymer is composed of ethene, propene, and at least one non-conjugated diene selected from the group of 1,4-hexadiene, dicyclopentadiene, ethylidene-norbornene, norbornadiene, and 1,5-hexadiene.

12. The composition of claim 1, wherein the Mooney (1+4) 125° C. value of the amorphous ethene-α-olefine copolymer ranges between 30 and 100.

13. The composition of claim 1, wherein the crystalline block copolymer has a melt index at 230° C. and 2.16 kg of between 0.1 and 20 dg/min.

14. The composition of claim 13, wherein said melt index is below about 10 decigrams per minute.

15. The composition of claim 1, further including 1–100 parts of carbon black incorporated per 100 parts of polymer mixture.

16. The composition of claim 1, wherein the amorphous ethene-α-alkene copolymer has a dsc crystallization temperature of at least 0° C.

17. The composition of claim 16, wherein said dsc crystallization temperature is higher than about 4° C.

18. The composition of claim 1, wherein the amorphous ethene-α-alkene copolymer has a heat of crystallization of at least about 6 cals/g.

19. The composition of claim 18, wherein said heat of crystallization is at least about 7 cals/gram.

20. The composition of claim 1, wherein the amorphous ethene-α-alkene polymer initiates crystallization below about 50° C., as measured by means of DSC.

21. The composition of claim 1, further including in said mixture a polyethene homopolymer in an amount of up to 25% by weight of said block copolymer.

22. A process for forming a thermoplastic, elastomeric composition based on a polyalkene rubber and a polyalkene plastic, which comprises mixing a preformed first component consisting essentially of
   (a) 25–85% by weight of a substantially amorphous ethene-α-alkene copolymer, having an X-ray crystallinity of below 4% by weight, a differential scanning (d. sc.) crystallization temperature of +0° C. to about 50° C. and a tensile strength in unvulcanized condition of at least 10 kg/cm$^2$,
with a second preformed component consisting essentially of
   (b) 15–75% by weight of an at least partially crystalline block copolymer of propene and ethene having an ethene content of between about 1 and 25% by weight and an X-ray crystallinity of at least 25% by weight.
by subjecting the components to shear forces at an elevated temperature between about 170° and about 200° C. form an intimate admixture of (a) and (b).

23. The process of claim 22, wherein the ethene content of the crystalline block copolymer is between about 2.5 to about 15% by weight.

24. The process of claim 22, wherein the substantially amorphous ethene-α-alkene copolymer has a maximum crystallinity of about 2.5% by weight.

25. The process of claim 22, wherein the amorphous ethene-α-alkene copolymer has an ethene content of between about 60 and about 80% by weight.

26. The process of claim 22, wherein the ethene-α-alkene copolymer has a tensile strength of at least about 50 kg/cm$^2$.

27. The process of claim 22, characterized in that the crystalline block copolymer of propene and ethene has been prepared by initial propene polymerization of propene, followed by ethene polymerization.

28. The process of claim 22, wherein the amorphous ethene-α-alkene copolymer is composed of ethene, propene, and a non-conjugated diene co-monomer.

29. The process of claim 22, wherein the Mooney (1+4) 125° C. value of the amorphous ethene-α-olefine copolymer ranges between 30 and 100.

30. The process of claim 22, wherein the crystalline block copolymer has a melt index at 230° C. and 2.16 kg of between 0.1 and 20 dg/min.

31. The process of claim 30, wherein the amorphous ethene-α-alkene copolymer is composed of ethene, propene, and at least one non-conjugated diene selected from the group of 1,4-hexadiene, dicyclopentadiene, ethylidene-norbornene, norbornadiene, and 1,5-hexadiene.

32. The process of claim 22, further including 1–100 parts of carbon black incorporated per 100 parts of polymer mixture.

33. The process of claim 22, further including mixing in a polyethene homopolymer is an amount of up to 25% by weight of said block copolymer.

* * * * *

UNITED STATES PATENT AND TRADEMARK OFFICE
CERTIFICATE OF CORRECTION

PATENT NO. : 4,272,431
DATED : June 9, 1981
INVENTOR(S) : Herman A. J. SCHEPERS

It is certified that error appears in the above-identified patent and that said Letters Patent are hereby corrected as shown below:

Claim 7, line 2, "or" should read -- of --.
Claim 7, line 3, after "polymerization" delete "of";
   line 4, delete "propene".

Claim 27, line 3, after "ploymerization" delete "of pro-";
   line 4, delete "pene".

Claim 31, line 1, delete "30" insert --22--.

Signed and Sealed this

Seventh Day of September 1982

[SEAL]

Attest:

GERALD J. MOSSINGHOFF

Attesting Officer    Commissioner of Patents and Trademarks